(12) United States Patent
Garcia Lerma et al.

(10) Patent No.: US 11,191,763 B2
(45) Date of Patent: Dec. 7, 2021

(54) HIV POST-EXPOSURE PROPHYLAXIS (71) Applicant: THE UNITED STATES OF AMERICA, as represented by the Secretary, Department of Health and Human Services, Bethesda, MD (US)

(72) Inventors: Jose Gerardo Garcia Lerma, Decatur, GA (US); Ivana Mabel Massud, Atlanta, GA (US); Walid M. Heneine, Atlanta, GA (US)

(73) Assignee: The United States of America as represented by the Secretary, Department of Health and Human Services, Bethesda, MD (US)

( * ) Notice: Subject to any disclaimer, the term of this patent is extended or adjusted under 35 U.S.C. 154(b) by 66 days.

(21) Appl. No.: 16/494,696

(22) PCT Filed: Mar. 19, 2018

(86) PCT No.: PCT/US2018/023152
§ 371 (c)(1),
(2) Date: Sep. 16, 2019

(87) PCT Pub. No.: WO2018/175325
PCT Pub. Date: Sep. 27, 2018

(65) Prior Publication Data
US 2020/0101072 A1 Apr. 2, 2020

Related U.S. Application Data (60) Provisional application No. 62/473,799, filed on Mar. 20, 2017.

(51) Int. Cl.
| | | |
|---|---|---|
| *A61K 31/513* | (2006.01) | |
| *A61P 31/18* | (2006.01) | |
| *A61K 31/47* | (2006.01) | |
| *A61K 31/5377* | (2006.01) | |
| *A61K 31/675* | (2006.01) | |

(52) U.S. Cl.
CPC ............ *A61K 31/513* (2013.01); *A61K 31/47* (2013.01); *A61K 31/5377* (2013.01); *A61K 31/675* (2013.01); *A61P 31/18* (2018.01)

(58) Field of Classification Search
CPC .................................................. A61K 31/513
See application file for complete search history.

(56) References Cited

U.S. PATENT DOCUMENTS

| | | |
|---|---|---|
| 9,044,509 B2 | 6/2015 | Henine et al. |
| 2015/0105350 A1 | 4/2015 | Ramanathan |
| 2017/0000807 A1 | 1/2017 | Koziara et al. |

FOREIGN PATENT DOCUMENTS

WO WO 2013/116720 A1 8/2013

OTHER PUBLICATIONS

Sax et al., Tenofovir alafenamide versus tenofovir disoproxil fumarate, coformulated with elvitegravir, cobicistat, and emtricitabine, for initial treatment of HIV-1 infection: two randomised, double-blind, phase 3, non-inferiority trials, Lancet, Jun. 27, 2015;385(9987): 2606-15, Epub Apr. 15, 2015.*
Massud et al., Chemoprophylaxis With Oral Emtricitabine and Tenofovir Alafenamide Combination Protects Macaques From Rectal Simian/Human Immunodeficiency Virus Infection, The Journal of Infectious Diseases, vol. 214, Issue 7, Oct. 1, 2016, pp. 1058-1062.*
Garcia-Lerma et al, Intermittent prophylaxis with oral truvada protects macaques from rectal SHIV infection, Sci. Trans. Med. 2: 14ra, 9 pages, Jan. 13, 2010.*
Coffey, "TAF: New data on tenofovir alafenamide fumarate," printed from http://hivinsite.ucf.edu/insite?page=hmp-1510-03 3 pages (printed on Nov. 21, 2016).
Garcia-Lerma et al., "Intermittent prophylaxis with oral truvada protects macaques from rectal SHIV infection," *Sci Transl Med* 2(14): 14ra4, 8 pages (Jan. 13, 2010).
Garcia-Lerma, "Chemoprophylaxis With Oral FTC/TAF Protects Macaques From Rectal SHIV Infection," *Conference on Retroviruses and Opportunistic Infections (CROI)*, 2 pages, printed from web, http://www.croiwebcasts.org/portal:jsessionid= B0AD4975A0A1C39AD035F9F802FBE5B0 (Feb. 2016).
Imaz and Podzamczer, "Tenofovir alafenamide, emtricitabine, elvitegravir, and cobicistat combination therapy for the treatment of HIV," *Expert Review of Anti-Effective Therapy* 15(1-6): 195-209 (2017).
Inciarte et al., "Tenofovir disoproxil fumarate/emtricitabine plus ritonavir-boosted lopinavir or cobicistat-boosted elvitegravir as a single-tablet regimen for HIV post-exposure prophylaxis," *J Antimicrob Chemother* 72: 2857-2861 (Jul. 25, 2017).
International Search Report and Written Opinion from parent PCT Application No. PCT/US2018/023152, 10 pages (Jun. 14, 2018).
Irvine et al., "Efficacy of HIV postexposure prophylaxis: systematic review and meta-analysis of nonhuman primate studies," *Clinical Infectious Diseases* 60(Suppl 3): S165-S169 (2015).

(Continued)

*Primary Examiner* — Svetlana M Ivanova
(74) *Attorney, Agent, or Firm* — Klarquist Sparkman, LLP (57) ABSTRACT

Disclosed is the use of a nucleoside reverse transcriptase inhibitor, a nucleotide reverse transcriptase inhibitor, and an integrase inhibitor after exposure to a potential human immunodeficiency virus (HIV) infection to inhibit or prevent an HIV infection. In some embodiments, a pharmacologically effective amount of emtricitabine (FTC), a pharmacologically effective amount of tenofovir alafenamide (TAF) or tenofovir disoproxil fumarate (TDF), a pharmacologically effective amount of the integrase inhibitor elvitegravir (EVG), and optionally cobistat (COBI) are used to inhibit or prevent an HIV infection, wherein these agents are administered only after a potential exposure to HIV. In specific non-limiting examples, only one or two doses of the anti-retroviral viral agents are administered to a subject after the potential exposure to HIV.

28 Claims, 1 Drawing Sheet

(56) References Cited

OTHER PUBLICATIONS

Massud et al., "Pharmacokinetic profile of raltegravir, elvitegravir and dolutegravir in plasma and mucosal secretions in rhesus macaques," *Antimicrob Chemother* 270: 1473-1481 (Jan. 27, 2015).

Mayer et l., "Optimal HIV postexposure prophylaxis pegimen pompletion with single tablet daily elvitegravir/cobicistat/tenofovir disoproxil fumarate/emtricitabine compared with more frequent dosing regimens," *J Acquir Immune Defic Syndr* 75(5): 535-539 (Aug. 15, 2017).

Molina et al., "On-demand preexposure prophylaxis in men at High Risk for HIV-1 infection," *N Engl J Med* (2015).

Prescribing Information for GENVOYA®, *Gilead Sciences*, 51 pages (Sep. 2016).

Ruone et al., "HIV-1 evolution in breakthrough infections in a human trial of oral pre-exposure prophylaxis with emtricitabine and tenofovir disoproxil fumarate," *J Acquir Immune Defic Syndr* 72(2): 129-132 (Jun. 1, 2016).

Sultan et al., "Current perspectives in HIV post-exposure prophylaxis," *HIV/AIDS—Research and Palliative Care* 6: 147-158 (2014).

Valin et al., "Evaluation of tolerability with the co-formulation elvitegravir, cobicistat, emtricitabine, and tenofovir disoproxil fumarate for post-HIV exposure prophylaxis," *BMC Infectious Diseases* 16: 718, 5 pages, (2016).

Garcia-Lerma et al., "Intermittent prophylaxis with oral Truvada protects macaques from rectal SHIV infection," *Science Translational Medicine* 2(14): 14ra4, 9 pages (Jan. 13, 2010).

Garcia-Lerma et al., "Prevention of rectal SHIV transmission in macaques by daily or intermittent prophylaxis with emtricitabine and tenofovir," *PLOS Medicine* 5(2): e28, 0291-0299 (Feb. 5, 2008).

Massud et al., "Lack of prophylactic efficacy of oral Maraviroc in macaques despite high drug concentrations in rectal tissues," *Journal of Virology* 87: 8952, 2013.

Massud et al., "Chemoprophylaxis with oral emtricitabine and tenofovir alafenamide combination protects macaques from rectal simian/human immunodeficiency virus infection," *Journal of Infectious Diseases* 214: 1058-1062 (Oct. 1, 2016).

Massud et al., "Efficacy of oral tenofovir alafenamide/emtricitabine combination or single-agent tenofovir alafenamide against vaginal simian human immunodeficiency virus infection in macaques," *Journal of Infectious Diseases* 220: 1826-1833 (Dec. 1, 2019).

Radizo et al., "Prevention of vaginal SHIV transmission in macaques by a coitally-dependent Truvada regimen," *PLOS One* 7(12): e50632, 8 pages (Dec. 4, 2012).

\* cited by examiner

HIV POST-EXPOSURE PROPHYLAXIS

CROSS REFERENCE TO RELATED APPLICATION

This is a § 371 U.S. national stage of International Application No. PCT/US2018/023152, filed Mar. 19, 2018, which claims the benefit of U.S. Provisional Application No. 62/473,799, filed Mar. 20, 2017, which is herein incorporated by reference in its entirety.

FIELD

This disclosure generally relates to a process for inhibiting initial infection by a retrovirus such as human immunodeficiency virus (HIV), and in particular to a combination of antiviral drugs useful in post-exposure prophylaxis against an immunodeficiency virus infection.

BACKGROUND

Despite the fact that significant progress has been made slowing the advancement of the symptoms of AIDS associated with HIV infection, in the absence of an effective vaccine, HIV continues to spread globally with an estimated 2.1 million new infections occurring in 2015. Antiretroviral therapy of HIV-infected persons resulting in durable HIV suppression has been shown to significantly reduce transmissibility of HIV. However, this approach cannot provide protection from HIV-infected persons who are undiagnosed, untreated, or virologically unsuppressed. Antiretroviral prophylaxis has been advanced as a strategy to prevent HIV acquisition among persons at high risk of HIV infection.

Daily oral pre-exposure prophylaxis (PrEP) with the combination emtricitabine (FTC) and tenofovir disoproxil fumarate (TDF) (the combination is sold as TRUVADA®) is recommended by CDC and WHO for the prevention of HIV in persons at high risk of infection. However, many people find it challenging to adhere to a daily dosing schedule and cannot fully benefit from PrEP. The availability of a potent HIV prevention pill that does not require daily dosing and can prevent infection if taken on-demand (before or after high-risk sexual activity) may be more cost effective, increase adherence, and reduce risks of drug toxicity. U.S. Pat. No. 9,044,509 was issued to the CDC in 2015 for a method of protecting a primate host against HIV infection by administering FTC in combination with tenofovir or TDF.

Post-exposure prophylaxis (PEP) methods are also in use, but they generally require the administration of anti-viral drug combinations for a prolonged period of time (usually 28 days). Although these PEP protocols have reduced the incidence of seroconversion following exposure to HIV, they require clinicians for administration and management for each potential HIV exposure adding cost and complexity. In addition, many patients experience significant adverse drug reactions during prolonged periods of drug administration or are otherwise unable to continue the treatment for the full 28 day period. It would be advantageous to have a highly effective but simple treatment regimen that can be self-administered by the user exclusively after an exposure to HIV within a wide dosing window.

SUMMARY

Methods are disclosed herein for protecting a primate from a self-replicating infection by an immunodeficiency virus without the necessity of prolonged pre-exposure or post-exposure administration of an anti-viral agent. Specifically, it is disclosed that co-administration of a nucleoside reverse transcriptase inhibitor, a nucleotide reverse transcriptase inhibitor, and an integrase inhibitor after a potential exposure of a subject to a potential immunodeficiency virus infection can inhibit or prevent an immunodeficiency virus infection. In further embodiments a pharmacoenhancer can also be co-administered to the subject.

Disclosed are methods for post-exposure prophylaxis that are of use to prevent or inhibit an immunodeficiency virus infection in a subject. In some embodiments, a prophylactically effective amount of FTC, a prophylactically effective amount of a tenofovir prodrug, such as but no limited to, tenofovir alafenamide (TAF) or TDF, a prophylactically effective amount of elvitegravir (EVG) and optionally a prophylactically effective amount of cobistat (COBI) are co-administered to inhibit or prevent an HIV infection in a subject, after a potential exposure of the subject to HIV. In specific non-limiting examples, only one or two doses of the anti-retroviral viral agents are co-administered to a subject after a potential exposure to HIV. The highly effective post-exposure prophylaxis methods disclosed herein are capable of avoiding the clinical drawbacks of daily doses of a pre-exposure prophylaxis regimen and prolonged administration of an anti-viral agent in a post-exposure prophylaxis regimen.

The foregoing and other objects, features, and advantages of the invention will become more apparent from the following detailed description, which proceeds with reference to the accompanying figures.

BRIEF DESCRIPTION OF THE DRAWINGS

FIG. 1 is a graph that documents post-exposure protection with a combination of FTC, TAF, EVG and COBI (FTC/TAF/EVG/COBI combo) in primates (Groups 1, 2, and 3). Rhesus macaques were exposed rectally to SHIV every two weeks and received FTC/TAF/EVG/COBI after each virus exposure. Animals from Group 1 (n=6) received two oral doses of FTC/TAF/EVG/COBI; the first dose was given 2 hours (h) after each virus exposure and the second dose was given 24 h later. Animals from Group 2 (n=5) received one oral dose of FTC/TAF/EVG/COBI 2 h after each virus exposure. Animals from Group 3 (n=6) received two oral doses of FTC/TAF/EVG/COBI; the first dose was given 24 h after each virus exposure and the second dose was given 24 h later. An additional group of 10 animals received placebo and were used as controls. Comparing the number of animals protected per group relative to placebo, each of the PEP modalities was found to have significantly lower proportion of infection. This figure shows that 5 of the 6 macaques from Group 1, 5 of the 5 macaques from Group 2, and 4 of the 6 macaques from Group 3 were protected against infection. In contrast, 9 of the 10 animals that received placebo were infected. The two-sided Fisher's exact p values are p=0.0020 for Group 1 (PEP+2 h/+24 h), p=0.0005 for Group 2 (PEP+2 h), and p=0.0110 for Group 3 (PEP+24 h/+48 h). An additional survival analysis was conducted to compare time to infection for the different regimens. The Kaplan-Meier graph in this figure shows all the treatment groups differed from the untreated control group over time. The two-sided Bonferroni-adjusted p-values are p=0.0008 for Group 1 (PEP+2 h/+24 h), p=0.0002 for Group 2 (PEP+2 h), and p=0.0065 for Group 3 (PEP+24 h/+48 h). The calculated efficacy of FTC/TAF/EVG/COBI in preventing infection was 90.4% for Group 1 (PEP+2 h/+24 h), 100% for Group 2 (PEP+2 h), and 70% for Group 3 (PEP+24 h/+48 h). Therefore, all the treatment groups showed increased survival when compared to the untreated control group.

DETAILED DESCRIPTION

Methods are disclosed herein for protecting a primate from a self-replicating infection by an immunodeficiency virus. These methods include co-administering to the primate a prophylactically effective amount of a nucleoside reverse transcriptase inhibitor, a nucleotide reverse transcriptase inhibitor, and an integrase inhibitor after exposure to a potential immunodeficiency virus infection. In further embodiments, the methods also include co-administering a pharmacoenhancer. In some embodiments, these agents are administered only after a potential exposure to an immunodeficiency retrovirus, such as HIV. Thus, in some embodiments these agents are not administered to the subject prior to the potential exposure to the immunodeficiency retrovirus, such as HIV. In specific non-limiting examples, the nucleoside reverse transcriptase inhibitor comprises FTC, the nucleotide reverse transcriptase inhibitor comprises TAF or TDF and the integrase inhibitor comprises EVG. In other non-limiting examples, the pharmacoenhancer comprises COBI.

I. Abbreviations

COBI: cobicistat
EVG: elvitegravir
FTC: 2'-deoxy-5-fluoro-3'thiacytidine, also known as emtricitabine
H: hours
HAART: highly active anti-retroviral therapy
HIV: human immunodeficiency virus
TAF: tenofovir alafenamide
TDF: tenofovir disoproxil fumarate
SIV: simian immunodeficiency virus
NARTI or NRTI: Nucleoside analog reverse-transcriptase
NtARTI or NtRTI: Nucleotide analog reverse-transcriptase inhibitors
PEP: Post-exposure prophylaxis
PrEP: Pre-exposure prophylaxis
Brief Summary of Terms Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "an agent" includes single or plural agents and can be considered equivalent to the phrase "at least one agent."

As used herein, the term "comprises" means "includes." Thus, "comprising an antigen" means "including an antigen" without excluding other elements.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

It is further to be understood that any and all base sizes or amino acid sizes, and all molecular weight or molecular mass values, given for nucleic acids or polypeptides are approximate, and are provided for descriptive purposes, unless otherwise indicated.

To facilitate review of the various embodiments, the following explanations of terms are provided:

Administration: The introduction of a composition into a subject by a chosen route. Administration can be local or systemic. For example, if the chosen route is o, the composition is administered by introducing the composition into a vein of the subject. As used herein, the term "co-administer" (or "co-administration") refers to administration of two or more agents within a 24-hour period of each other, for example, as part of a clinical treatment regimen. In other embodiments, "co-administer" refers to administration of two or more agents within 2 hours of each other. In other embodiments, "co-administer" refers to administration of two or more agents within 30 minutes of each other. In other embodiments, "co-administer" refers to administration of two or more agents within 15 minutes of each other. In other embodiments, "co-administer" refers to administration of two or more agents at the same time, either as part of a single formulation or as multiple formulations that are administered by the same or different routes. A single "dose" refers to co-administration at the same time.

Agent: Any substance or any combination of substances that is useful for achieving an end or result; for example, a substance or combination of substances useful for inhibiting or preventing an immunodeficiency virus, such as an HIV, infection in a subject. Agents include proteins, nucleic acid molecules, compounds, small molecules, organic compounds, inorganic compounds, or other molecules of interest. An agent can include a therapeutic agent (such as an anti-retroviral agent), a diagnostic agent or a pharmaceutical agent.

Animal: Living multi-cellular vertebrate organisms, a category that includes, for example, mammals and birds. The term mammal includes both human and non-human mammals. Similarly, the term "subject" includes both human and veterinary subjects. The term "primate" includes human and non-human primates, such as macaques and rhesus monkeys. Thus, a primate includes a monkey, baboon, chimpanzee, gorilla, and a human Nonhuman primates are appreciated to themselves be susceptible to infection by retroviruses and in particular immunodeficiency viruses and represent well-established animal models as to human response with an appreciation that physiological differences often require different doses in milligrams per kilogram for a nonhuman primate animal model relative to a human.

Anti-retroviral agent: An agent that specifically inhibits a retrovirus from replicating or infecting cells. Non-limiting examples of antiretroviral drugs include fusion inhibitors (e.g., enfuvirtide), entry inhibitors (e.g., maraviroc), nucleoside and nucleotide reverse transcriptase inhibitors (e.g., lamivudine, zidovudine, abacavir, tenofovir, TAF, TDF, FTC), protease inhibitors (e.g., indinavir, ritonavir, darunavir, atazanavir), and integrase inhibitors (e.g., elvitegravir, raltegravir, dolutegravir).

Anti-retroviral therapy (ART): A therapeutic treatment for HIV infection involving administration of at least one anti-retroviral agent (e.g., one, two, three or four anti-retroviral agents) to an HIV-infected individual during a course of treatment. One example of a regimen includes treatment with a combination of TAF, FTC, and EVG. In some examples, ART includes Highly Active Anti-Retroviral Therapy (HAART).

Cobicistat (COBI): 1,3-thiazol-5-ylmethyl (2R,5R)-(5-{[(2S)-2-[(methyl{[2-(propan-2-yl) 1,3-thiazol-4-yl]methyl]carbamoyl)amino]]-4-(morpholin-4-yl)butanamido}-1,6-diphenylhexan-2-yl)carbamate. Cobicistat is a cytochrome P450 3A inhibitor that acts as pharmacokinetic enhancer to increase the effectiveness of HIV anti-viral drugs. It is used to increase the bioavailability of other anti-retroviral agents. Cobicistat is marketed as TYBOST® and is also known as GS-9350.

Diurnal: Any pattern that recurs daily.

Effective amount: The amount of an agent (such as an anti-retroviral agent) that alone, or together with one or more additional agents, induces the desired response, such as an inhibition of an HIV infection.

Emtricitabine; 2'-deoxy-5-fluoro-3'thiacytidine (FTC). FTC is sold under the trade name EMTRIVA® (emtricitabine) formerly COVIRACIL®), is a nucleoside reverse transcriptase inhibitor (NRTI) used in the treatment of HIV infection in adults and children. Emtricitabine is also marketed in a fixed-dose combination with tenofovir disproxil fumerate (Viread) under the brand name TRUVADA®. A fixed-dose triple combination of emtricitabine, tenofovir and efavirenz (Sustiva, marketed by Bristol-Myers Squibb) was approved by the U.S. Food and Drug Administration (FDA) on Jul. 12, 2006 under the name ATRIPLA®. Emtricitabine makes up one fourth of the four drug ("Quad") combination known as STRIBILD®.

Human Immunodeficiency Virus (HIV): A retrovirus that causes immunosuppression in humans (HIV disease), and leads to a disease complex known as the acquired immunodeficiency syndrome (AIDS). "HIV disease" refers to a well-recognized constellation of signs and symptoms (including the development of opportunistic infections) in persons who are infected by an HIV virus, as determined by antibody or western blot studies. Laboratory findings associated with this disease include a progressive decline in T cells. HIV includes HIV type 1 (HIV-1) and HIV type 2 (HIV-2). Related viruses that are used as animal models include simian immunodeficiency virus (SIV), and feline immunodeficiency virus (FIV). Treatment of HIV-1 with ART has been effective in reducing the viral burden and ameliorating the effects of HIV-1 infection in infected individuals.

Inhibiting or treating a disease: Inhibiting the full development of a disease or condition, for example, in a subject who is at risk for a disease such as acquired immunodeficiency syndrome (AIDS). "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease.

Nucleoside analog reverse-transcriptase inhibitors (NRTIs): The initial class of antiretroviral drugs that was developed. In order to be incorporated into the viral DNA, NRTIs must be activated in the cell by the addition of phosphate groups to their deoxyribose moiety, to form NRTI triphosphates. This phosphorylation step is carried out by cellular kinase enzymes. NRTIs include zidovudine, didanosine, zalcitabine, stavudine, lamivudine, abacavir, and emtricitabine (also called FTC).

Nucleotide analog reverse-transcriptase inhibitors (NtRTIs): NTARTIs and NtRTIs are nucleotide analogues of cytidine, guanosine, thymidine, and adenosine that are of use in treatment of HIV infections. For example, tenofovir is an NtRTI adenosine analogue.

Pharmacoenhancer: A substance that increases the bioavailability and bioefficacy of active substances with which they are combined without having any activity of their own at the dose used. These agents are also known as "bioenhancers." Increased bioavailability means increased levels of an agent, such as in the blood. Increased bioefficacy means the increased effectiveness of the drug due to, at least in part, to increased bioavailability. COBI is a pharmacoenhancer.

Tenofovir Prodrugs: Tenofovir (9-R-[(2-phosphonomethoxy)propyl]adenine), an acyclic nucleotide analog of dAMP, is a potent in vitro and in vivo inhibitor of human immunodeficiency virus type 1 (HIV-1) replication. Tenofovir is sequentially phosphorylated in the cell by AMP kinase and nucleoside diphosphate kinase to the active species, tenofovir diphosphate, which acts as a competitive inhibitor of HIV-1 reverse transcriptase that terminates the growing viral DNA chain. Tenofovir disoproxil furnarate (TDF) is an oral prodrug of tenofovir, marketed as VIREAD®, that has received marketing authorization in many countries as a once-daily tablet (300 mg) in combination with other antiretroviral agents for the treatment of HIV-1 infection.

U.S. Pat. Nos. 7,390,791 and 7,803,788, both incorporated herein by reference, disclose prodrugs of phosphonate nucleotide analogs that are also useful in therapy. 9-[(R)-2-[[(S)-[[(S)-1-(isopropoxycarbonyl)ethyl]amino]phenoxyphosphinyl]-methoxy]propyl]adenine 16 is an isopropylalaninyl phenyl ester prodrug of tenofovir. Tenofovir alafenamide (TAF) is also known as GS-7340. TAF has been marketed under the name VEMLIDY®. The hemifumarate form of TAF is also of use in the methods disclosed herein. TAP exhibits potent anti-HIV activity 500- to 1000-fold enhanced activity relative to tenofovir against. HIV-1 in T cells, activated peripheral blood mononuclear lymphocytes (PBMCs), and macrophages. TAP also has enhanced ability to deliver and increase the accumulation of the parent tenofovir into PBMCs and other lymphatic tissues in vivo. TAP can be prepared as described in U.S. Pat. No. 7,390,791, incorporated herein by reference.

FTC/TAF/EVG/COBI, also called GENVOYA® (which contains 150 mg EVG, 150 mg COBI, 200 mg FTC, and 10 mg TAF) is approved for the treatment of an existing HIV infections in subjects. EVG, FTC and TAF have been shown to suppress viral reproduction. Cobicistat increases the effectiveness of the combination, such as by inhibiting the liver and gut wall enzymes that metabolize EVG. The use of FTC/TAF/EVG/COBI for treatment of an existing HIV infection is disclosed, for example, in U.S. Patent Publication U.S. 2015/0105350 entitled "Combination Therapy Comprising Tenofovir Alafenamide Hemifumarate and Cobicistat for Use in the Treatment of Viral Infections," which is incorporated herein by reference. A FTC/TAF/

EVG/COBI combination drug is manufactured, and is commercially available from, Gilead Sciences.

Therapeutic agent: Used in a generic sense, it includes treating agents, prophylactic agents, and replacement agents. A therapeutic agent is used to ameliorate a specific set of conditions in a subject with a disease or a disorder.

Therapeutically effective amount and prophylactically effective amount: A quantity of a specific substance, such as a disclosed agent, sufficient to achieve a desired effect in a subject being treated. A therapeutically effective amount can be the amount necessary to inhibit an immunodeficiency virus replication or treat AIDS in a subject with an existing infection with the immunodeficiency virus. "Prophylactically effective amounts" refers to administration of an agent (or combination) that inhibits or prevents establishment of a self-replicating infection with an infectious agent, such as an immunodeficiency virus, for example the Human Immunodeficiency Virus (HIV). Post-exposure prophylaxis (PEP) is the prevention or inhibition of an immunodeficiency virus infection, wherein the active agent(s) are administered after a potential exposure to an immunodeficiency virus such as HIV. The exposure can be recreational (sexual, drug related, etc.) or occupational (such as from a needle stick or contaminated blood product in the hospital setting). Pre-exposure prophylaxis (PrEP) is the prevention or inhibition of an immunodeficiency virus infection in a host, wherein the active agent(s) are administered prior to any possible infection (e.g., prior to any exposure) of the subject with the virus. "Protection" as used in the context of a host primate response to an immunodeficiency virus challenge is defined by the host primate being serologically negative and negative in a polymerase chain reaction (PCR) testing for viral genome.

Unit dosage form: A physically discrete unit, such as a capsule, tablet, or solution, that is suitable as a unitary dosage for a human patient, each unit containing a predetermined quantity of one or more active ingredient(s) calculated to produce a therapeutic effect, in association with at least one pharmaceutically acceptable diluent or carrier, or combination thereof. Unit dosage formulations contain a daily dose or an appropriate fraction thereof, of the active ingredient(s).

Virus: Microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-I and HIV-II), simian immunodeficiency virus (SIV), and feline immunodeficiency virus (FIV).

Suitable methods and materials for the practice or testing of this disclosure are described below. Such methods and materials are illustrative only and are not intended to be limiting. Other methods and materials similar or equivalent to those described herein can be used. For example, conventional methods well known in the art to which a disclosed invention pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., Current Protocols in Molecular Biology, Greene Publishing Associates, 1992 (and supplements to 2012); Ausubel et al., *Short Protocols in Molecular Biology: A Compendium of Methods from Current Protocols in Molecular Biology,* 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In case of conflict, the present specification, including explanations of terms, will control.

II. Description of Several Embodiments

The use of a combination of antiretroviral agents as a post-exposure prophylactic treatment is provided herein for inhibiting a retroviral infection, such as for providing protection against an HIV infection developing to a level of self-replicating infection. Retroviral transmission through most routes entails a new primate host receiving a small number of viral particles. This can be through an occupational or recreational exposure. Common routes of retrovirus transmission illustratively include sexual intercourse, medical worker skin puncture inoculation, hypodermic needle sharing, blood transfusions, inadvertent exposure to infected blood products, birth canal exposure, and breastfeeding. The disclosed methods provide a post-exposure prophylaxis (PEP) for protecting a primate from infection with an immunodeficiency retrovirus following a potential exposure from any route. In some embodiments, the disclosed methods are used in adults, such as humans 18 years or older, exposed occupationally or recreationally to an immunodeficiency virus infection.

The disclosed methods provide a PEP method for protecting a primate from infection with an immunodeficiency retrovirus following a potential exposure. Protection is achieved by co-administering to the primate a combination of a pharmacologically effective amount of the nucleoside reverse transcriptase inhibitor, such as, but not limited to, FTC, a pharmacologically effective amount of the nucleotide reverse transcriptase inhibitor, such as, but not limited to, tenofovir or a tenofovir prodrug such as, but not limited to, TAF or TDF, and a pharmacologically effective amount of an integrase inhibitor, such as, but not limited to, EVG. This combination can be co-administered with or without a pharmacoenhancer, such as, but not limited to, COBI. In some embodiments, the co-administration is oral. Pharmaceutically acceptable salts and related forms of the active agent agents can also be used in the disclosed methods. In specific non-limiting examples, only one or two doses of these agents is/are administered to a subject following a potential exposure and/or one or more doses of these agents are not administered to the subject diurnally prior to this exposure. For example, the subject is not taking a daily pre-exposure dose, as in a PrEP regimen.

In some embodiments, a prophylactically effective amount of nucleoside reverse transcriptase inhibitor, such as, but not limited to, FTC a prophylactically effective amount of the nucleotide reverse transcriptase inhibitor, such as, but not limited to, a tenofovir prodrug such as TDF or TAF, and a prophylactically effective amount of the integrase inhibitor, such as EVG, can be formulated in a single composition, such as in a unit dose. Optionally, a prophylactically effective amount of a pharmacoenhancer, such as COBI, is included in this same composition. In some embodiments, the composition can be formulated for oral administration. Thus, these active agents can be combined into a single unit dose and administered to the subject of interest.

The doses of individual active components are administered in prophylactically effective amounts, to create a therapeutic concentration of the active composition at the situs of retrovirus initial founder cell population infection. It is appreciated that establishing an effective concentration at the time of viral replication for a given active agent in the target cells, includes factors for the agent such as the route of administration, pharmacokinetics, absorption rate based on administration route, effects of food on oral absorption, in vivo distribution, metabolic pathways, elimination route, race, gender, and age of the subject, single dose incident side effects, long term administration side effects, and synergistic effects with co-administered active agents. Information related to these factors considered in dosing are available from the United States Food and Drug Administration (fda.gov/oashi/aids/virals.html). In some embodiments, the dosing according to the present methods utilize as a starting point the maximal recommended tolerated dosing levels for the given active agent combination associated with HAART treatment protocols.

U.S. Published Patent Application No. 2015/0105350, incorporated herein by reference, discloses the use of FTC, TAF and other tenofovir prodrugs, EVG, and COBI for the treatment of HIV infections. As disclosed in this published patent application the oral dose of TAF can be in the range from about 0.0001 to about 100 mg/kg body weight per day, for example, from about 0.01 to about 10 mg/kg body weight per day, from about 0.01 to about 5 mg/kg body weight per day, from about 0.5 to about 50 mg/kg body weight per day, from about 1 to about 30 mg/kg body weight per day, from about 1.5 to about 10 mg/kg body weight per day, or from about 0.05 to about 0.5 mg/kg body weight per day. As a non-limiting example, the daily candidate dose for an adult human of about 70 kg body weight will range from about 0.1 mg to about 1000 mg, or from about 1 mg to about 1000 mg, or from about 5 mg to about 500 mg, or from about 1 mg to about 150 mg, or from about 5 mg to about 150 mg, or from about 5 mg to about 100 mg, or about 10 mg, and may take the form of single or multiple doses. In one embodiment, the oral dose of TAF may be in the form of a combination of agents (e.g., TAF/FTC/EVG/COBI).

When COBI or a pharmaceutically acceptable salt thereof is combined with certain specific solid carrier particles (e.g. silica derivatives), the resulting combination possesses improved physical properties. For example, the resulting combination has low hygroscopicity as compared to COBI alone. Additionally, the resulting combination is a free-flowing powder, with high loading values for COBI, acceptable physical and chemical stability, rapid drug release properties, and excellent compressibility. Thus, the resulting combination can readily be processed into solid dosage forms (e.g. tablets). Thus, COBI can be used with any suitable solid carrier, provided the resulting combination has physical properties that allow it to be more easily formulated than the parent compound. For example, suitable solid carriers include kaolin, bentonite, hectorite, colloidal magnesium-aluminum silicate, silicon dioxide, magnesium trisilicate, aluminum hydroxide, magnesium hydroxide, magnesium oxide and talc. In one embodiment of the invention, the solid carrier can comprise calcium silicate or magnesium aluminometasilicate. COBI can be coated in the pores and on the surface of a solid carrier. Suitable silica derivatives of use are disclosed in PCT Publication WO 03/037379, incorporated herein by reference.

Exemplary dosages of use in the disclosed methods are (1) COBI: 10-500 mg, 50-500 mg, 75-300 mg, 100-200 mg, or 150 mg; (2) TAF: 1-60 mg, 3-40 mg, 5-30 mg, 8-20 mg, or 10 mg; (3) FTC: 10-500 mg, 50-500 mg, 75-300 mg, 150-250 mg, or 200 mg; and (4) EVG: 10-500 mg, 50-500 mg, 75-300 mg, 100-200 mg, or 150 mg. Tenofovir can be used in amounts of less than 300 mg, 200 mg or less and 100 mg or less. COBI can be used in amounts of 50-500 mg, 100-400 mg, 100-300 mg, and 150 mg.

Tenofovir (or a prodrug thereof, such as but not limited to, TDF or TAF) and COBI or pharmaceutically acceptable salt(s) thereof, can be co-administered. Tenofovir (or TDF, TAF, or another prodrug), COBI, FTC, and EVG can be co-administered. Tenofovir (or TDF, TAF, or another prodrug) and COBI can be co-administered in a single pharmaceutical composition. Tenofovir (or TDF, TAF, or another prodrug), COBI, FTC, and EVG can be co-administered in a single pharmaceutical composition. One of skill in the art will know that, in the case of administering a pharmaceutically acceptable salt or complex of an agent, the amount administered will be adjusted relative to the weight of the component added to produce the salt or complex.

The method can include co-administering 200 mg of FTC and 150 mg of EVG. The method can include co-administering 150 mg COBI, 100 mg or less tenofovir, 150 mg EVG, and 200 mg FTC. The method can include co-administering 150 mg COBI, 200 mg or less tenofovir, 150 mg EVG, and 200 mg FTC. The method can include co-administering 150 mg COBI, less than 300 mg tenofovir, 150 mg EVG, and 200 mg FTC. The method can include co-administering 150 mg COBI, 50 mg tenofovir, 150 mg EVG, and 200 mg FTC. In some specific non-limiting example, the method can include co-administering 150 mg EVG, 150 mg COB, 200 mg FTC, and 10 mg TAF. These compositions can be administered orally. See U.S. Published Patent Application No. 2015/0105350, incorporated herein by reference for additional dosing information. In some embodiments, GENOYA® is administered to the primate.

The active agents may be administered to a primate, such as a human, in any conventional manner. While it is possible for the active agents to be administered as raw compounds, they are preferably administered as one or more pharmaceutical compositions. The salt, carrier, or diluent should be acceptable in the sense of being compatible with the other ingredients and not deleterious to the recipient thereof. Examples of carriers or diluents for oral administration include cornstarch, lactose, magnesium stearate, talc, microcrystalline cellulose, stearic acid, povidone, crospovidone, dibasic calcium phosphate, sodium starch glycolate, hydroxypropyl cellulose (e.g., low substituted hydroxypropyl cellulose), hydroxypropylmethyl cellulose (e.g., hydroxypropylmethyl cellulose 2910), and sodium lauryl sulfate. The pharmaceutical compositions can be prepared by any suitable method, such as those methods well known in the art of pharmacy, for example, methods such as those described in Gennaro et al., Remington's Pharmaceutical Sciences (18th ed., Mack Publishing Co., 1990), especially Part 8: Pharmaceutical Preparations and their Manufacture.

Such methods include the step of bringing into association the active agents with the carrier or diluent and optionally one or more accessory ingredients. Such accessory ingredients include those conventional in the art, such as, fillers, binders, excipients, disintegrants, lubricants, colorants, flavoring agents, sweeteners, preservatives (e.g., antimicrobial preservatives), suspending agents, thickening agents, emulsifying agents, and/or wetting agents. The pharmaceutical compositions of use in the methods disclosed herein can provide controlled, slow release or sustained release of the active agents over a period of time. The controlled, slow release or sustained release of the agents can maintain the agents in the bloodstream of the human for a longer period of time than with conventional formulations.

Pharmaceutical compositions include, but are not limited to, coated tablets, pellets, solutions, powders, capsules, and dispersions in a medium that is insoluble in physiologic fluids, or where the release of the therapeutic compound follows degradation of the pharmaceutical composition due to mechanical, chemical, or enzymatic activity. For oral administration, fine powders or granules may contain diluting, dispersing, and or surface active agents and may be present, for example, in water or in a syrup, in capsules or sachets in the dry state, or in a non-aqueous solution or suspension wherein suspending agents may be included, or in tablets wherein binders and lubricants may be included. When administered in the form of a liquid solution or suspension, the formulation may contain one or more active ingredients and purified water. Optional components in the liquid solution or suspension include suitable sweeteners, flavoring agents, preservatives (e.g., antimicrobial preservatives), buffering agents, solvents, and mixtures thereof. A component of the formulation may serve more than one function. For example, a suitable buffering agent also may act as a flavoring agent as well as a sweetener. Suitable sweeteners include, for example, saccharin sodium, sucrose, and mannitol. A mixture of two or more sweeteners may be used. The sweetener or mixtures thereof are typically present in an amount of from about 0.001% to about 70% by weight of the total composition. Suitable flavoring agents may be present in the pharmaceutical composition to provide a flavor to make the pharmaceutical composition easier for a human to ingest. The flavoring agent or mixtures thereof are typically present in an amount of about 0.0001% to about 5% by weight of the total composition.

Preservatives can also be present in the composition. Suitable preservatives include, for example, methylparaben, propylparaben, sodium benzoate, and benzalkonium chloride. A mixture of two or more preservatives may be used. The preservative or mixtures thereof are typically present in an amount of about 0.0001% to about 2% by weight of the total composition. Buffering agents can also be present in the compositions. Suitable buffering agents include, for example, citric acid, sodium citrate, phosphoric acid, potassium phosphate, and various other acids and salts. A mixture of two or more buffering agents may be used. The buffering agent can be present in an amount of about 0.001% to about 4% by weight of the total composition.

A solvent can be used when a liquid suspension is desirable. Suitable solvents for a liquid solution or suspension include, for example, sorbitol, glycerin, propylene glycol, and water. A mixture of two or more solvents may be used. The solvent or solvent system can present in an amount of about 1% to about 90% by weight of the total composition. These types of formulations are disclosed, for example, in U.S. Published Patent Application No. 2015/0105350, which is incorporated herein by reference.

In some embodiments, only a limited number of doses of the therapeutic agents are co-administered to a primate following a potential exposure to the immunodeficiency retrovirus. In specific non-limiting examples, only 1, 2, 3, 4 or 5 doses of the therapeutic agents are co-administered the primate following a potential exposure to the immunodeficiency retrovirus. In further non-limiting examples, only one or two doses of the therapeutic agents are co-administered to the primate following a potential exposure to the immunodeficiency retrovirus.

In additional embodiments, doses of the active agents, e.g., TAF/TDF, FTC, EVG and optionally COBI, are co-administered to the primate only after a potential exposure to the immunodeficiency virus. In some non-limiting examples, doses of these agent are not co-administered to the primate prior to the potential exposure to the immunodeficiency retrovirus. In yet other embodiments, these agents are not co-administered to the subject diurnally prior to the potential exposure. Thus, in some embodiments, the primate has not been co-administered TAF/TDF, FTC, EVG, and optionally COBI, such as diurnally, prior to the potential exposure to the immunodeficiency retrovirus. In some non-limiting examples, the primate has not been co-administered TAF/TDF, FTC, EVG, and optionally COBI, such as diurnally, for at least 1, 2, 3, 4, 5, 6, 7, 8, 9, 10, 14, 30, 60, 90 or 120 days prior to the potential exposure to the immunodeficiency retrovirus.

In some embodiments, the present methods utilize doses of agents. In further embodiments, active agents (such as TAF/TDF, FTC, EVG and optionally COBI) co-administered to a subject at specific time points, such as within about 72, 48, or 24 hours after a potential exposure. In some embodiments, each dose can include oral co-administration of FTC, TAF/TDF, and EVG. In other embodiments, each dose can include oral co-administration of FTC, TAF/TDF, EVG and COBI. In specific non-limiting examples, each dose includes TAF.

In some non-limiting examples, 1, 2, 3, 4, 5 or 6 doses are co-administered to the subject within 72, 48 or 24 hours of a potential exposure. In some non-limiting examples, at least one dose is co-administered to the subject within 72, 48 or 24 hours after a potential exposure. In other non-limiting examples, at least one dose can be co-administered to the subject within about 48 hours, or within about 24 hours, after the potential exposure to the immunodeficiency retrovirus. In further non-limiting examples, only one dose is co-administered to the subject within about 48 hours after the potential exposure to the immunodeficiency retrovirus. In yet other non-limiting examples, two doses are co-administered to the subject within about 48 hours after the potential exposure to the immunodeficiency retrovirus.

In some non-limiting examples, only one dose is co-administered to the subject within about 24 hours after the potential exposure to the immunodeficiency retrovirus. In additional non-limiting examples, two doses are co-administered to the subject within about 24 hours after the potential exposure to the immunodeficiency retrovirus. In further non-limiting examples, two doses are co-administered to the subject within about 24 hours after the potential exposure to the immunodeficiency retrovirus, such as at about 2 hours after the potential exposure and at 24 hours after the potential exposure to the immunodeficiency retrovirus.

In some non-limiting examples, the methods include co-administering a first dose to the subject within 24 hours and co-administering a second dose between about 24 hour and about 48 hours after the potential exposure to the immunodeficiency retrovirus. For example, the methods can include co-administering a first dose at about 24 hours after the potential exposure to the immunodeficiency retrovirus, a second at about 48 hours after the potential exposure to the immunodeficiency retrovirus. In other non-limiting examples, the methods can include co-administering a first dose at about 48 hours after the potential exposure to the immunodeficiency retrovirus, and a second dose at about 72 hours after the potential exposure to the immunodeficiency retrovirus. In other non-limiting examples, the method can include co-administering an additional dose between about 2 and about 12 hours after the potential exposure to the immunodeficiency retrovirus.

In further non-limiting examples, the method can include co-administering a first dose at 2, 3, 4, 5, 6, 7, 8, 9, 10, 11 or 12 hours after the potential exposure to the immunodeficiency retrovirus, and co-administering a second dose to the subject 24, 25, 26, 27, 28, 29, 30, 31, 32, 33, 34, 35, 36, 37, 38, 39, 40, 41, 42, 43, 44, 45, 46, 47, or 48 hours after the potential exposure to the immunodeficiency retrovirus. In some embodiments, the method can include co-administering a dose at about 2 hours after the potential exposure to the immunodeficiency retrovirus and co-administering a second dose at about 24 or 48 hours after the potential exposure to the immunodeficiency retrovirus. In yet other embodiments, the methods include co-administering a single dose at 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 hours after the potential exposure to the immunodeficiency retrovirus. In further non-limiting examples, the method can include co-administering a first dose at 24, 25, 24, 27, 28, 29, 30, 31, 31, 33, 34, 35, 36, 37, 38, 39, 30, 41, 42, 43, 44, 45, 46, 47, or 48 hours after the potential exposure to the immunodeficiency retrovirus, and co-administering a second dose to the subject 70, 71, 72, 73, 74, 75, 76, 77, 78, 79, 80, 81, 82, 83 or 84 hours after the potential exposure to the immunodeficiency retrovirus.

In some embodiments, a dose(s) is/are not administered diurnally to the subject prior to the potential exposure to the immunodeficiency retrovirus. Thus, in some embodiments, dose(s) are administered to the subject only after the potential exposure to the immunodeficiency retrovirus. When active agents in the dose are not co-administered, such as diurnally, to the subject before the potential exposure with the immunodeficiency virus, the subject has not been exposed to active agents in the dose, for example, at least 1, 2, 3, 4, 5, 6, 7, 8, 19 10, 11 or 12 months prior to the potential exposure, or for at least 1, 2, 3, 4, 5, 6, 7, 8, 9, 10, 11, 12, 13, 14, 30, 60, 90 or 120 days prior to the potential exposure to the immunodeficiency retrovirus. In some embodiments, each dose can include oral co-administration of FTC, TAF/TDF, and EVG. In other embodiments, each dose can include oral co-administration of FTC, TAF/TDF, EVG and COBI. In specific non-limiting examples, TAF is included in the dose(s).

In some embodiments, methods are disclosed for protecting a primate from a self-replicating infection by an immunodeficiency virus, including co-administering to the primate a prophylactically effective amount of FTC, TAF/TDF, and EVG, after exposure to a potential immunodeficiency virus infection. In some non-limiting examples, the FTC, the TAF and the EVG are administered orally to the primate. The method can include co-administering a pharmacoenhancer, such as COBI to the primate. In some non-limiting examples, the pharmacoenhancer is administered orally to the primate. The primate can be a human. The immunodeficiency retrovirus can be HIV, such as HIV-1 or HIV2.

In further embodiments, co-administering comprises a total of 1 or 2 oral doses of FTC, TAF, EVG and COBI after the potential exposure to the immunodeficiency retrovirus. In some non-limiting examples, the FTC, TAF, EVG and COBI only after the potential exposure to the immunodeficiency virus. In other non-limiting examples, co-administering comprises a total of 1 or 2 oral doses of FTC, TAF, EVG and COBI after the potential exposure to the immunodeficiency retrovirus.

Disclosed are several dosing regimens of use. In some embodiments, co-administering comprises co-administering at least one dose of FTC, TAF, EVG and COBI within about 48 hours after the potential exposure to the immunodeficiency retrovirus. In a non-limiting example, co-administering includes co-administering only one dose of the FTC, TAF, EVG and COBI within about 48 hours after the potential exposure to the immunodeficiency retrovirus. In some embodiments, co-administering FTC, TAF, EVG and COBI includes co-administering at least one dose within about 24 hours after the potential exposure to the immunodeficiency retrovirus. In further mon-limiting examples, co-administering FTC, TAF, EVG and COBI comprises co-administering only one dose within 24 hours after the potential exposure to the immunodeficiency retrovirus.

In other embodiments, the methods include co-administering one dose within 24 hours or within 12 hours after the potential exposure to the immunodeficiency retrovirus, and a second dose of FTC, TAF, EVG and COBI between about 24 hour and about 48 hours after the potential exposure to the immunodeficiency retrovirus. In more embodiments, the methods include administering one dose between about 2 and 12 hours of the potential exposure to the immunodeficiency virus, and further co-administering an additional dose between about 24 and about 48 hours after the potential exposure to the immunodeficiency retrovirus. In more embodiments, the methods include administering one dose between about 24 and 48 hours of the potential exposure to the immunodeficiency virus, or at about 2 hours after the potential exposure to the immunodeficiency retrovirus and further co-administering an additional dose at 24 or 48 hours after the potential exposure to the immunodeficiency retrovirus. In non-limiting examples, the method includes co-administering two doses to the primate, wherein a) one dose is co-administered to the primate at about 2 hours after the potential exposure to the immunodeficiency retrovirus, a second dose is co-administered to the primate at about 24 hours after the potential exposure to the immunodeficiency retrovirus; b) one dose is co-administered to the primate at about 24 hours after the potential exposure to the immunodeficiency retrovirus, a second dose is co-administered to the primate at about 48 hours after the potential exposure to the immunodeficiency retrovirus; or c) one dose is co-administered to the primate at about 48 hours after the potential exposure to the immunodeficiency retrovirus, a second dose is co-administered to the primate at about 72 hours after the potential exposure to the immunodeficiency retrovirus.

In further embodiments, FTC, TAF, and EVG are co-administered in a single pharmaceutical composition. In other embodiments, FTC, TAF, EVG and COBI are co-administered in a single pharmaceutical composition. In some embodiments, the pharmaceutical composition comprises 150 mg EVG, 150 mg COBI, 200 mg FTC, and 10 mg TAF.

In some embodiments, a PEP method of protecting a primate from a self-replicating infection by an immunodeficiency virus is provided. The method includes co-administering to the primate a prophylactically effective amount of a pharmaceutical composition comprising FTC, TAF, EVG, and (COBI after exposure to a potential immunodeficiency virus infection, wherein the pharmaceutical composition is not administered prior to the exposure, and wherein only one or two doses of the pharmaceutical composition is administered to the primate. In some embodiments, only one dose of the pharmaceutical composition is administered to the subject about 24 to about 48 hours after the potential exposure. In further embodiments, one dose of the pharmaceutical composition is administered within about 24 hours after the potential exposure. In additional embodiments, two doses of the pharmaceutical composition are administered to the subject. The subject can be a human, and the immunodeficiency retrovirus can be a human immunodeficiency retrovirus (HIV). The HIV can be HIV-1 or HIV-2. In further embodiments, the pharmaceutical composition comprises 150 mg EVG, 150 mg COBI, 200 mg FTC, and 10 mg TAF.

In some embodiments, one dose of the pharmaceutical composition is administered within about 24 hours of the potential exposure and another dose of the pharmaceutical composition is administered about 24 to about 48 hours after the potential exposure. In more non-limiting examples, one dose of the pharmaceutical composition is administered at about 2 hours after the potential exposure and a second dose of the pharmaceutical composition is administered at about 24 hours after the potential exposure.

A pharmaceutical composition is also provided, wherein the pharmaceutical composition includes a prophylactically effective amount of FTC, TAF, EVG and COBI and is of use in the methods disclosed herein.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

EXAMPLES

Previous work in macaque models indicated that there were challenges with identifying post-exposure prophylaxis regimens. An oral combination of FTC and TDF given two hours after rectal virus exposure and a second dose 24 h later provided protection (75.6%). However, no protection was found when a more potent regimen of tenofovir and FTC was given subcutaneously 24 h after rectal virus challenge and a second dose 48 h after this challenge (Garcia-Lerma et al. Science Translational Medicine 2010 2:14ra4). It is disclosed herein that combined administration, including an HIV integrase inhibitor that acts at later stages of the virus replicative cycle, extends the window of protection. The higher potency of these regimens ensures high efficacy and provides a long window for self-administration.

The prophylactic efficacy of a combination of FTC, TAF, EVG and COBI was investigated to determine protection from infection with simian HIV (SHIV) in macaques. This regimen, also called GENVOYA® (which contains 150 mg EVG, 150 mg COBI, 200 mg FTC, and 10 mg TAF) is approved for treating HIV infected persons. This regimen is referred to below as FTC/TAF/EVG/COBI. A validated repeat virus exposure rectal SHIV transmission model, that had previously predicted the efficacy of daily oral PrEP with TRUVADA® (FTC/TDF) in humans, was used in these studies. Macaques were exposed rectally to simian HIV (SHIV) once every two weeks for a total of 8 exposures, and received FTC/TAF/EVG/COBI orally after each viral exposure. A first group of 6 animals received one dose of FTC/TAF/EVG/COBI 2 h after virus exposure and a second dose 24 h later (Group 1; +2 h/+24 h regimen). A second group of 5 animals received one dose of FTC/TAF/EVG/COBI 2 h after each virus exposure (Group 2; +2 h regimen). These strategies mimic an "after-sex" post-exposure prophylaxis regimen initiated shortly after a potential HIV exposure in humans. It differs from the TRUVADA® pre-exposure PrEP regimen in which dosages were administered daily before and after potential exposure to HIV. It also differs from other recommended post-exposure prophylaxis regimens in which the anti-viral drugs are typically administered for a period of 28 days or more.

Figure 1:
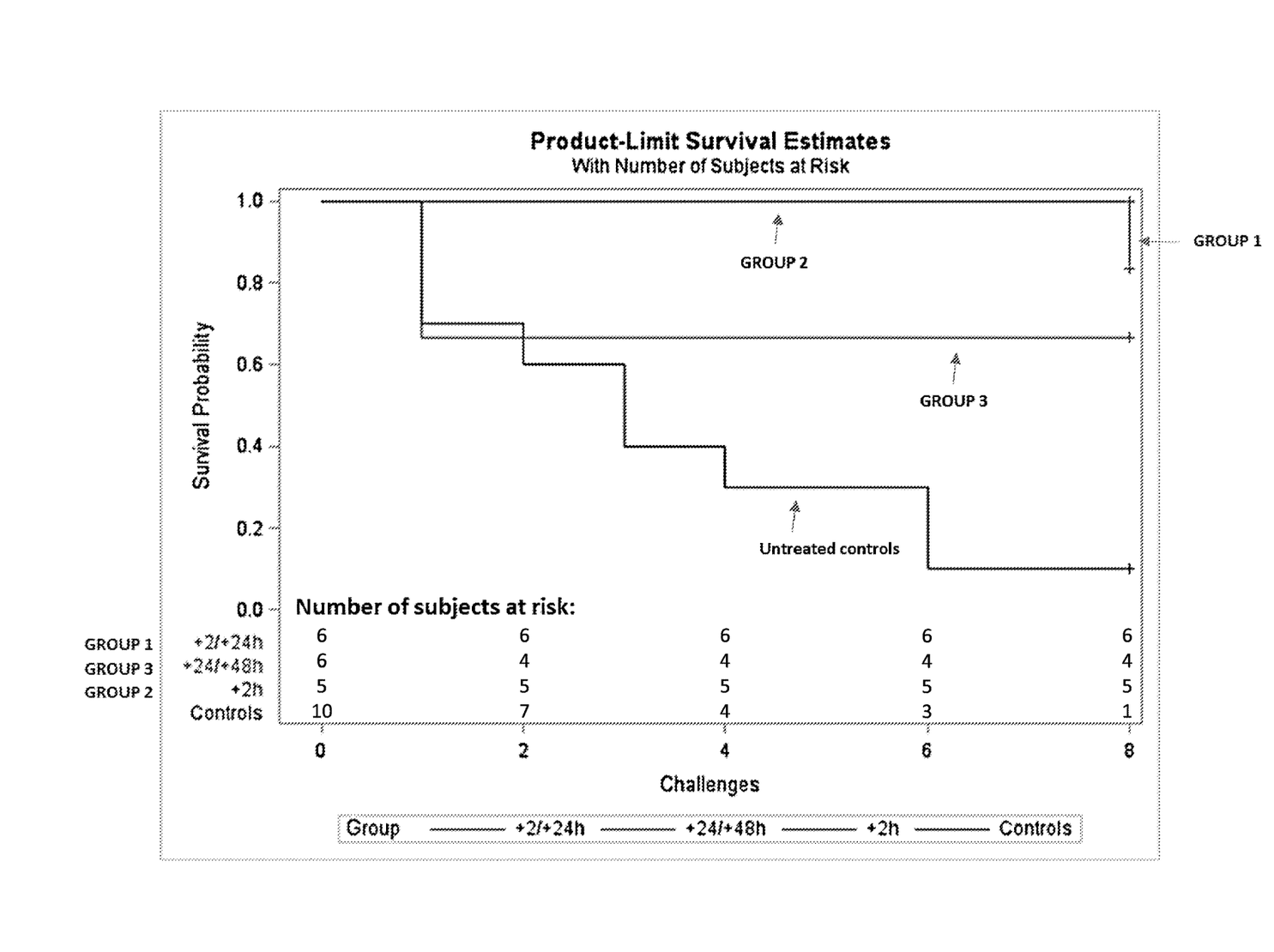

FIG. 1 shows that 10 of the 11 macaques that received FTC/TAF/EVG/COBI were protected against infection; five macaques from Group 1 (+2 h/+24 h regimen) and 5 macaques from Group 2 (+2 h regimen). In contrast to the treated animals, 9 of the 10 untreated controls were infected during this period of time. Each of the treatment groups was found to have a significantly lower proportion infected compared to the control group. The two-sided Fisher's exact p values are p=0.0020 for Group 1 (+2 h/+24 h regimen) and p=0.0005 for Group 2 (+2 h regimen). An additional survival analysis was conducted to compare time to infection for the different regimens. The Kaplan-Meier graph in FIG. 1 shows that the two treatment groups differed from the untreated control group over time. The two-sided Bonferroni-adjusted p-values are p=0.0008 for Group 1 (+2 h/+24 h regimen) and p=0.0002 for Group 2 (+2 h regimen). Hence purely post-exposure administration of one or two doses of FTC/TAF/EVG/COBI was highly effective in preventing infection, with a calculated efficacy of 90%-100%.

Example 2

Additional Studies

To confirm the utility of FTC/TAF/EVG/COBI in preventing sexual HIV infection as a self-administered "after-sex" pill (post-exposure prophylaxis or PEP), an experimental approach was designed that included the use of the macaque model of repeated rectal virus exposures. Macaques (n=6) were exposed rectally to SHIV once every 2 weeks for a total of 8 exposures, and received two doses of FTC/TAF/EVG/COBI orally after each virus exposure. The first dose was given 24 h after exposure and the second dose was given 24 h later (Group 3; +24 h/+48 h regimen). The number of animals protected was compared relative to placebo. The treatment group was found to have a significantly lower proportion infected compared to the control group. The two-sided Fisher's exact p value is p=0.0110. An additional survival analysis was conducted to compare time to infection. The Kaplan-Meier graph in FIG. 1 shows the treatment group differed from the untreated control group over time. The two-sided Bonferroni-adjusted p-is p=0.0065.

The results showed that there was significant protection against a simian immunodeficiency virus infection using all of the tested treatment regimens. These studies evidenced that FTC/TAF/EVG/COBI provides protection against HIV infection, and can be of use when self-administered as an "after sex" PEP.

We claim:

1. A method of protecting a primate from a self-replicating infection by an immunodeficiency virus, comprising:

co-administering to the primate a total of 1 or 2 doses of a prophylactically effective amount of emtricitabine (FTC), a prophylactically effective amount of tenofovir alafenamide (TAF), and a prophylactically effective amount of elvitegravir (EVG) within about 48 hours after exposure to a potential immunodeficiency virus infection, wherein the primate is serologically negative and wherein the FTC, TAF and EVG are administered only after the exposure to the potential immunodeficiency virus.

2. The method of claim 1, further comprising co-administering a pharmacoenhancer.

3. The method of claim 2, wherein the pharmacoenhancer comprises cobicistat (COBI).

4. The method of claim 1, wherein the FTC, the TAF and the EVG are administered orally to the primate.

5. The method of claim 2, wherein the pharmacoenhancer is administered orally to the primate.

6. The method of claim 3, wherein co-administering comprises a total of 1 or 2 oral doses of FTC, TAF, EVG and COBI after the potential exposure to the immunodeficiency retrovirus.

7. The method of claim 6, wherein co-administering comprises co-administering only one dose of the FTC, TAF, EVG and COBI within about 48 hours after the potential exposure to the immunodeficiency retrovirus.

8. The method of claim 6, wherein co-administering FTC, TAF, EVG and COBI comprises co-administering at least one dose within about 24 hours after the potential exposure to the immunodeficiency retrovirus.

9. The method of claim 6, wherein co-administering FTC, TAF, EVG and COBI comprises co-administering only one dose within 24 hours after the potential exposure to the immunodeficiency retrovirus.

10. The method of claim 8, further comprising co-administering a second dose of FTC, TAF, EVG and COBI between about 24 hour and about 48 hours after the potential exposure to the immunodeficiency retrovirus.

11. The method of claim 8, further comprising co-administering an additional dose between about 2 and about 12 hours after the potential exposure to the immunodeficiency retrovirus.

12. The method of claim 8, comprising co-administering an additional dose at about 2 hours after the potential exposure to the immunodeficiency retrovirus.

13. The method of claim 6, comprising co-administering two doses to the primate, wherein a) one dose is co-administered to the primate at about 2 hours after the potential exposure to the immunodeficiency retrovirus, a second dose is co-administered to the primate at about 24 hours after the potential exposure to the immunodeficiency retrovirus; or b) one dose is co-administered to the primate at about 24 hours after the potential exposure to the immunodeficiency retrovirus, a second dose is co-administered to the primate at about 48 hours after the potential exposure to the immunodeficiency retrovirus.

14. The method of claim 1, wherein the FTC, TAF, and EVG are co-administered in a single pharmaceutical composition.

15. The method of claim 3, wherein the FTC, TAF, EVG and COBI are co-administered in a single pharmaceutical composition.

16. The method of claim 15, wherein the pharmaceutical composition comprises 150 mg elvitegravir, 150 mg cobicistat, 200 mg emtricitabine, and 10 mg tenofovir alafenamide.

17. The method of claim 1, wherein the subject is human, and the immunodeficiency retrovirus is a human immunodeficiency retrovirus (HIV).

18. The method of claim 17, wherein the HIV is HIV-1.

19. A post-exposure prophylaxis (PEP) method of protecting a primate from a self-replicating infection by an immunodeficiency virus, comprising:
co-administering to the primate a prophylactically effective amount of a pharmaceutical composition comprising emtricitabine (FTC), tenofovir alafenamide (TAF), elvitegravir (EVG), and cobicistat (COBI) after exposure to a potential immunodeficiency virus infection, wherein the pharmaceutical composition is not administered prior to the exposure, wherein the primate is serologically negative, and wherein only one or two total doses of the pharmaceutical composition is administered to the primate within about 72 hours after exposure.

20. The PEP method of claim 19, wherein only one dose of the pharmaceutical composition is administered to the subject about 24 to about 48 hours after the potential exposure.

21. The PEP method of claim 19, wherein the only one dose of the pharmaceutical composition is administered within about 24 hours after the potential exposure.

22. The PEP method of claim 19, wherein two doses of the pharmaceutical composition are administered to the subject.

23. The PEP method of claim 22, wherein one dose of the pharmaceutical composition is administered within about 24 hours of the potential exposure and another dose of the pharmaceutical composition is administered about 24 to about 48 hours after the potential exposure.

24. The PEP method of claim 23, wherein one dose of the pharmaceutical composition is administered at about 2 hours after the potential exposure and a second dose of the pharmaceutical composition is administered at about 24 hours after the potential exposure.

25. The PEP method of claim 19, wherein one dose of the pharmaceutical composition is administered within about 48 hours of the potential exposure and another dose of the pharmaceutical composition is administered about 48 to about 72 hours after the potential exposure.

26. The PEP method of claim 19, wherein the primate is a human, and wherein the immunodeficiency retrovirus is a human immunodeficiency retrovirus (HIV).

27. The PEP method of claim 25, wherein the HIV is HIV-1.

28. The PEP method of claim 19, wherein the pharmaceutical composition comprises 150 mg EVG, 150 mg COBI, 200 mg FTC, and 10 mg TAF.

* * * * *